United States Patent [19]

Cavell et al.

[11] Patent Number: 5,352,813

[45] Date of Patent: Oct. 4, 1994

[54] CARBONYLATION OF METHANOL USING A NOVEL TRANSITION METAL CATALYST

[75] Inventors: Ronald G. Cavell, Edmonton, Canada; Kattesh V. Katti, Columbia, Mo.

[73] Assignee: University of Alberta, Edmonton, Canada

[21] Appl. No.: 752,348

[22] Filed: Sep. 3, 1991

Related U.S. Application Data

[63] Continuation-in-part of Ser. No. 575,903, Aug. 31, 1990, abandoned.

[51] Int. Cl.$^5$ .................. C07F 15/00; C07F 9/02; C07C 51/12
[52] U.S. Cl. .................. 556/21; 556/137; 556/138; 502/159; 502/166; 502/167; 562/519; 568/14; 568/17; 560/232
[58] Field of Search .................. 556/21, 137, 138; 502/159, 166, 167; 562/519; 568/14, 17; 560/232

[56] References Cited

U.S. PATENT DOCUMENTS

| | | | |
|---|---|---|---|
| 3,769,329 | 10/1973 | Paulik et al. | 260/488 K |
| 3,951,857 | 4/1976 | McCoy et al. | 252/428 |
| 4,400,548 | 8/1983 | Abatjoglou et al. | 568/454 |
| 4,429,165 | 1/1984 | Wegman | 568/487 |
| 4,491,675 | 1/1985 | Abatjoglou et al. | 568/454 |
| 4,522,933 | 6/1985 | Abatjoglou et al. | 502/161 |
| 4,593,011 | 6/1986 | Abatjoglou et al. | 502/161 |
| 4,599,206 | 7/1986 | Billig et al. | 558/85 |
| 4,668,651 | 5/1987 | Billig et al. | 502/158 |
| 4,670,570 | 6/1987 | Wegman et al. | 556/18 |
| 4,716,250 | 12/1987 | Abatjoglou et al. | 568/454 |
| 4,717,775 | 1/1988 | Billig et al. | 568/454 |
| 4,727,200 | 2/1988 | Wegman et al. | 568/902 |
| 4,731,486 | 3/1988 | Abatjoglou et al. | 568/454 |
| 4,737,588 | 4/1988 | Billig et al. | 556/12 |
| 4,748,261 | 5/1988 | Billig et al. | 556/404 |
| 4,769,498 | 9/1988 | Billig et al. | 568/454 |
| 4,789,753 | 12/1988 | Billig et al. | 558/85 |

FOREIGN PATENT DOCUMENTS

| | | |
|---|---|---|
| 0124160 | 7/1984 | European Pat. Off. . |
| 0185882 | 2/1986 | European Pat. Off. . |
| 0335765 | 10/1989 | European Pat. Off. . |

OTHER PUBLICATIONS

Katti et al., Organometallics, vol. 7, pp. 2236–2238 (1988).
Cavell et al., Phosphorus, Sulfur and Silicon, vol. 41, pp. 43–50 (1989).
Cavell et al., Sixth International Symposium on Homogeneous Catalysis, Aug. 21–26, 1988, Vancouver, B.C.
Katti et al., "Two Novel Rhodium (I) Metallacycles . . . ", Organometallics, 1988, 7, 2236.
Katti et al., "First Examples of an Isometric Methylene-Bridged Free Phosphano . . . ", Inorganic Chemistry, 1989, 28, 413.
Katti et al., "New Approaches to Heteroatom Chelation . . . ", Organometallics, 1989, 8, 2147.
Maley et al., "Rhodium Catalyzed Reduction Carbonylation of Methanol", Organometallics, 1989, 8, 2883–2892.
Wegman et al., J. Chem. Soc., Chem. Commun., 1987, 1891.

*Primary Examiner*—Jose' G. Dees
*Assistant Examiner*—Porfirio Nazario
*Attorney, Agent, or Firm*—Millen, White, Zelano & Branigan

[57] ABSTRACT

An improved process is provided for the carbonylation of methanol to acetic acid and/or its derivatives, especially methyl acetate, under mild reaction conditions using a novel catalyst precursor. The precursor is a transition metal complex having a heterodifunctional bidentate phosphorus—nitrogen ligand attached to the metal. The carbonylation reaction can now typically be carried out at 80° C. and CO pressure of 40 p.s.i.g.

19 Claims, No Drawings

CARBONYLATION OF METHANOL USING A NOVEL TRANSITION METAL CATALYST

CROSS-REFERENCE TO RELATED APPLICATION

This application is a C-I-P of application Ser. No. 07/575,903, filed Aug. 31, 1990, now abandoned, the disclosure of which is hereby incorporated by reference.

FIELD OF THE INVENTION

The invention relates to transition metal catalyst precursors having a heterodifunctional bidentate phosphorus-nitrogen ligand attached to the metal. It further relates to the use of such precursors in the carbonylation of methanol, typically to produce methyl acetate, acetic acid and acetic anhydride.

BACKGROUND OF THE INVENTION

The homologation, hydroformylation and carbonylation reactions of methanol to produce carbon oxygenates are well documented.

The homologation reaction is exemplified by the reaction of methanol with synthesis gas (a mixture of carbon monoxide and hydrogen) to produce ethanol namely:

$$CH_3OH + CO + 2H_2 \rightarrow CH_3CH_2OH + H_2O$$

The reaction typically is conducted in the presence of a CO/Ru—I catalyst, at elevated temperatures and pressures (up to 10,000 p.s.i.g.).

However, in U.S. Pat. No. 4,727,200 there is disclosed an alcohol homologation reaction wherein methanol is reacted with synthesis gas in contact with a rhodium/ruthenium, iodine, diphosphine catalyst system.

The hydroformylation (or reductive carbonylation) reaction is exemplified by the reaction of methanol with synthesis gas to form acetaldehyde:

$$CH_3OH + CO + H_2 \rightarrow CH_3CHO + H_2O$$

Typically, a Co—I or Rh—I—PR$_3$ catalyst is utilized, again at elevated temperatures and pressures.

Tertiary polyphosphine monoxide ligands are used in the hydroformylation processes described in the following patents:

U.S. Pat. No. 4,429,165:
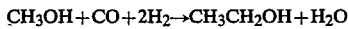

U.S. Pat. No. 4,400,548
U.S. Pat. No. 4,522,933
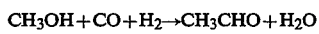

U.S. Pat. No. 4,593,011
U.S. Pat. No. 4,491,675
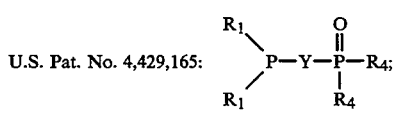

Additionally, the use of phosphite ligands in hydroformylation processes is taught in the followings patents:

U.S. Pat. No. 4,599,206
U.S. Pat. No. 4,717,775
U.S. Pat. No. 4,737,588
U.S. Pat. No. 4,789,753
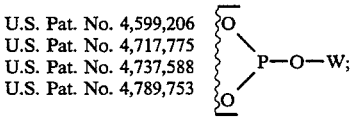

U.S. Pat. No. 4,668,651
U.S. Pat. No. 4,769,498
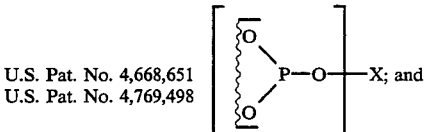

U.S. Pat. No. 4,748,261
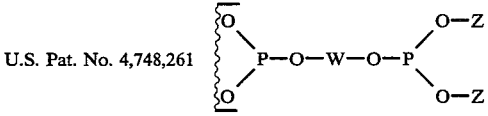

Further hydroformylation processes using sulphonated tertiary phosphine ligands are described in U.S. Pat. Nos. 4,716,250 and 4,731,486.

The carbonylation reaction is exemplified by the reaction of methanol with carbon monoxide to form acetic acid or methyl acetate, depending on the solvent used.

$$CH_3OH + CO \xrightarrow{(H_2O)} CH_3COOH$$

$$2CH_3OH + CO \xrightarrow{(CH_3OH)} CH_3-\overset{O}{\underset{\|}{C}}-O-CH_3 + H_2O$$

In U.S. Pat. No. 3,769,329, issued to F. E. Paulik et. al. there is disclosed a carbonylation process which comprises reacting methanol with carbon monoxide at 175° C. and 1000 p.s.i.g. to form acetic acid. This process is illustrative of existing industrial conditions for conducting the reaction.

U.S. Pat. No. 4,670,570, issued to Wegman et. al. details a process for the production of carboxylic acids from alcohols using rhodium complex catalysts.

More specifically, the catalyst comprises:

Rh(CO)X(R′R″PGZ)

wherein

Z is selected from the group consisting of:

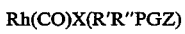

and G represents one of the following two groups:

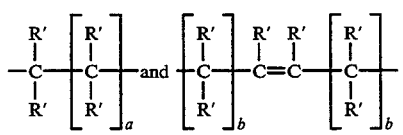

The Wegman reaction conditions are mild, typically involving reaction temperatures less than about 130° C. and a reaction pressure less than about 250 p.s.i.g.

SUMMARY OF THE INVENTION

In accordance with one aspect of the present invention, there is provided novel transition metal catalyst precursors having a phosphorus-nitrogen chelated ligand attached to the metal.

Preferably the metal is a Group VIII B transition metal, most preferably one of Rh, Ni or Co.

The chelated ligand comprises a substantially unreactive connecting backbone structure which links two different dative centers or a donor with an anionic site. In one preferred embodiment, the connecting backbone structure comprises a saturated hydrocarbon entity $(CH_2)_n$, wherein $n=1-5$, or a branched alkyl such as $(CH_3)CH$, connected between a phosphine or an arsine and a pentavalent phosphorous of an iminatophosphorane. Alternatively, the connecting backbone structure comprises an unsaturated entity such as a benzene ring connected in the o-positions to the phosphine or arsine and the phosphorus of the iminatophosphorane. In another alternative, the backbone is an olefin

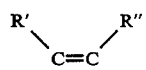

connected across the olefin bond to the phosphine or arsine and the phosphorus of the iminatophosphorane.

Preferably the transition metal catalyst precursor is of the general formulae I, II or III:

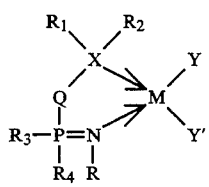

(I)

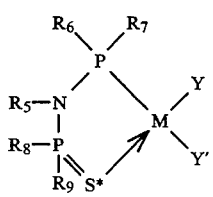

(II)

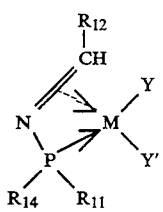

(III)

wherein:

M is Group VIII B transition metal

Y,Y' are same or different, selected from CO, Cl⁻, phosphines and olefinic hydrocarbons $R_{1-4}$, $R_{6-12}$ are same or different non-reactive substituents Q is selected from $(CH_2)_n$ where $n=1-5$, a benzene ring connected to P and X in the o-positions, an olefin connected to P and X across the double bond, and $(CH_3)CH$ X is P or As R = a substituted aromatic ring

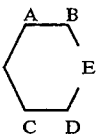

where A, B, C or D are selected from F, H, $NO_2$ and alkyl and E is endocyclic nitrogen or a C—CN group, or isomers thereof or $R = SiMe_3$ or $TiCl_2Cp$ where Me is methyl, and Cp is cyclopentadiene $R_5$ is aryl or alkyl, and $S^*$ is S, Se, O or N—R, R being as defined hereinabove.

Most preferably, the transition metal M in the catalyst precursor is Rh, Co or Ni and the substituents $R_{1-4}$ and $R_{6-12}$ are substituted or unsubstituted aryl groups. Preferred catalyst precursors of the formula I are those in which X is P, R is the substituent wherein A, B, C and D are selected from F and $NO_2$ and Q is $(CH_2)_n$, a benzene ring, the olefin $R'C=CR''$ ($R',R''=H,CH_3$...), or $(CH_3)CH$. Preferred catalyst precursors of the formula II are those in which $R_5$ is phenyl or methyl and $S^*$ is S, Se or NR where R is as defined above. Preferred catalyst precursors of the formula III are those in which $R_{10-12}$ are selected from hydrogen, phenyl or substituted phenyl groups.

The combination of the specific elements in the catalyst precursor results in an efficacious catalyst system which has been found to be active under mild conditions for catalysis of the carbonylation of methanol to acetic acid and its derivatives.

Without being bound by the following, it is believed that the heterodifunctional character of the bidentate phosphorus-nitrogen ligand provides a complex in which the unequal binding of the phosphorus and the nitrogen to the metal results in the preferential dissociation of the more weakly bound coordinating atom, so as to provide a reactive site at the metal. The unreactive backbone of the ligand keeps the dissociated element readily available for recombination, so as to facilitate the cyclical nature of the catalytic process. Thus in the case of the Rh(I) complex, catalytic carbonylation of methanol to acetic acid and/or its derivatives proceeds under mild conditions of temperature and pressure because the facile dissociation of nitrogen appears to allow coordination of molecular CO to the rhodium centre to form the reactive species.

In the specific case of Rh(I) catalysis, it is believed that the Rh(I) centre is oxidatively converted to a Rh(III) complex and that the adduct provides the vehicle for catalytic transformation. Dissociation of the nitrogen substituent and coordination of free CO in this case forms a complex which appears to subsequently undergo internal rearrangement to an acyl substituted Rh complex. Upon removal of the acyl substituent, the uncoordinated nitrogen, which is held to the metal compound by the coordinated phosphorus and the backbone structure of the ligand molecule, is in a suitable position to coordinate to the Rh centre and stabilize the catalytic unit so that the cycle may be continued.

In a second broad aspect of the invention it has been discovered that the above-described catalyst precursors are active as catalysts in the known carbonylation reaction to methanol. Surprisingly, the carbonylation reaction catalyzed with the catalyst precursors of this invention takes place under very much milder conditions than had heretofore been reported. Conditions comprising temperatures of 25°–200° C., and pressures of 1 to 5000 p.s.i.g. are operative. More specifically, the reaction may be conducted at a temperature as low as about 50°–120° C., preferably about 80° C. and a pressure of about 40–400 p.s.i.g., preferably about 40 p.s.i.g.

Without being bound by same it is believed that, in respect of catalyst precursors of the formula I, the choice of an activated R-substituent bound to nitrogen, particularly a fluoroaromatic compound, allows one to 'fine tune' the catalyst so as to selectively control the carbonylation reaction.

In another aspect of the invention, it has been discovered that the carbonylation of methanol with carbon monoxide can further be promoted using a reagent that enhances the oxidative addition of methyl iodide to the metal center, thereby accelerating the reaction. Examples of such promotors are lithium acetate, sodium tetraphenyl borate, $Ph_4AsCl$, $LiCl$, $LiI$, $KPF_6$, $Et_3N$, pyridine, quinoline, morpholine, the Bezman salt

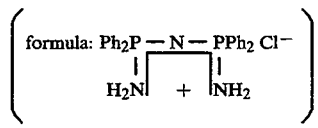

and similar compounds.

Broadly stated then, in a catalyst aspect, the invention comprises a transition metal catalyst precursor of the general formulae I, II and III, having a phosphorus-nitrogen chelated ligand attached to the metal.

Broadly stated, in a process aspect the invention is an improvement in a catalytic process for carbonylation of methanol to acetic acid and/or its derivatives. The improvement comprises reacting the methanol and carbon monoxide using a transition metal catalyst precursor having a phosphorus-nitrogen chelated ligand attached to the metal as a catalyst.

DESCRIPTION OF THE PREFERRED EMBODIMENT

In accordance with the best mode of the present invention, a process is provided which uses a novel rhodium complex catalyst precursor for the carbonylation reaction of methanol to form acetic acid and its derivatives such as methylacetate. However Ni, Co and Ir have also been shown to work. Thus the transition metal M in the catalyst precursor is preferably selected from the Group VIII B transition metals Fe, Co, Ni, Ru, Rh, Pd, Os, Ir and Pt. In using the catalyst precursor it is possible to conduct the carbonylation reaction under particularly mild and hence more energy efficient conditions.

The reaction conditions for carrying out the carbonylation process of this invention can be those heretofore conventionally used and may comprise a reaction temperature from about 25° C. to 200° C. and pressure from about 1 to 5000 p.s.i.g. However the preferred carbonylation process will be that which is most efficient in producing methyl acetate and/or acetic acid from $CH_3OH$. The optimization of the reaction conditions needed to achieve the best conversion, efficiency and catalyst life will be within the knowledge of one skilled in the art and easily assessed by following the preferred embodiments of this invention as described in detail below or in the experimental section.

As stated, the reaction temperature may range between 25° C. and 200° C. The preferred temperature is in the range between 50° C. to 120° C. The CO pressure will range from 1 p.s.i.g. to 5,000 p.s.i.g. The preferred pressure is between 40 to 400 p.s.i.g. The reaction time will range from 30 minutes to several hours.

Exemplary ligands employable are those having the general formulae:

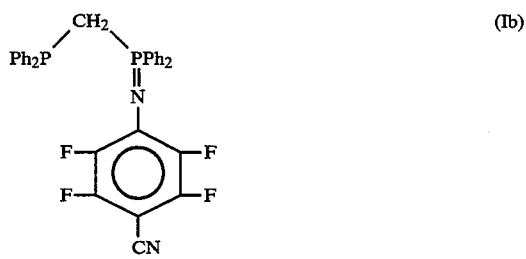

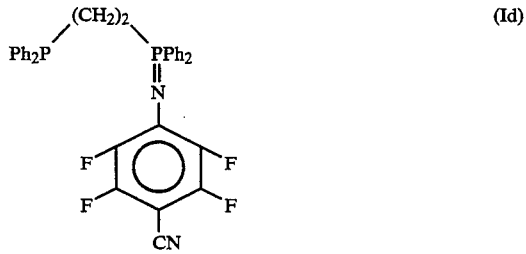

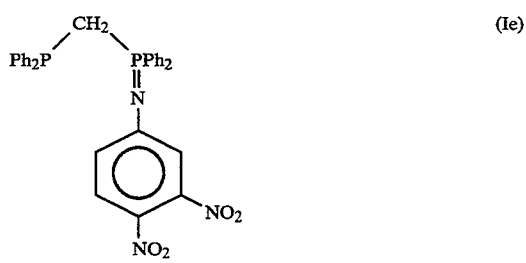

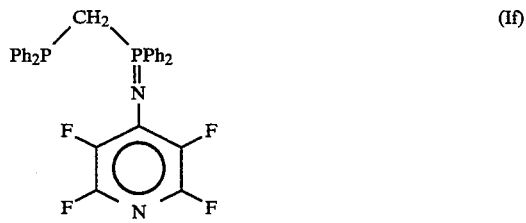

-continued
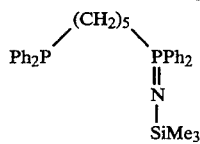 (Ih)
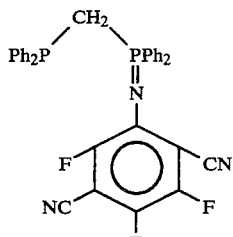 (Ii)
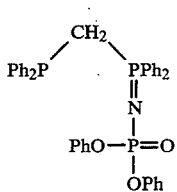 (Ij)
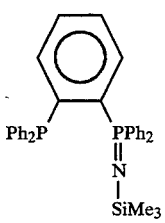 (Ik)
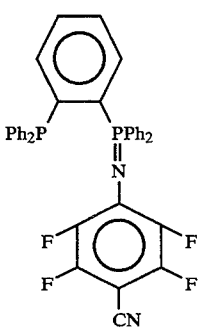 (Il)
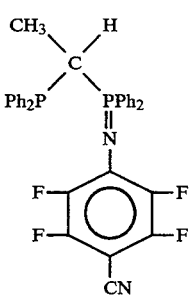 (Im)
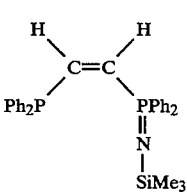 (In)
-continued
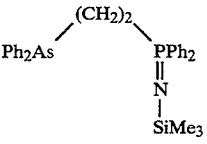 (Io)
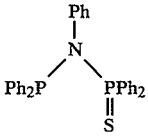 (IIa)
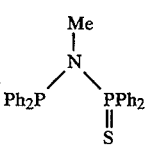 (IIb)
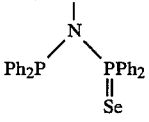 (IIc)
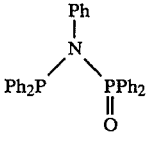 (IId)
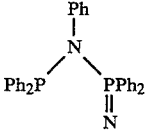 (IIe)
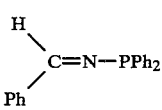 (IIIa)
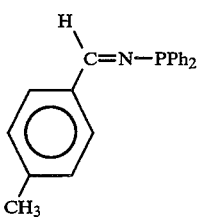 (IIIb)
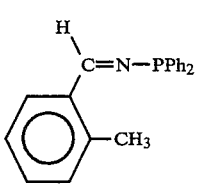 (IIIb)
and the like.
The phenyl groups in the above compounds are generally illustrative of substituted or unsubstituted aryl groups which may be used as the $R_{1-4}$ and $R_{6-12}$ substituents in the catalyst precursors.

The substituents Y,Y' in the catalyst precursor depend on the form in which the transition metal is included in the catalyst precursor synthesis or on the form in which the transition metal is added in the carbonylation reaction. Typically, Y and Y' will be coordinating neutral molecules such as CO, phosphine or olefins such as cyclooctadiene, or bound anions such as halides ($Cl^-$ being the preferred halide) and acetate.

In the conversion reaction it is to be noted that an excess of ligand is used. It is possible that the excess ligand can be the heterodifunctional ligand or a suitable phosphine, such as triphenylphosphine. It has been observed that the use of excess heterodifunctional ligand provides better turnover numbers compared to when a phosphine is used as the excess ligand, proving the superiority of the difunctional ligands.

To effect the conversion of methanol to acetic acid, methyl acetate etc., the catalytic precursor can be added to the system either in the form of a metal complex prepared by the procedures described in detail in the experimental section or can be added as the transition metal precursor and the ligand, thus preparing the complex in-situ. The Rh metal can be added in any of several forms including $[Rh(CO)_2Cl]_2$, $[Rh(Cod)Cl]_2$ and the Co and Ni in the form of acetates or as other suitable salts.

Most of the reactions have been carried out using methanol itself as the solvent. However other solvents like methyl acetate, which is the product from the carbonylation of methanol, acetophenone or similar solvents can be employed for carrying out the reaction.

Under the reaction conditions employed, lower concentrations of the catalyst provide higher turnover numbers. However adjustment of the reaction conditions should yield higher turnover numbers and good reaction rates at higher concentrations of the catalyst. The concentration may range from 25 to 2,000 ppm transition metal and more preferably from about 50 to 1,000 ppm calculated as free metal.

The following examples are illustrative of the present invention and are not to be regarded as limitative.

EXPERIMENTAL

All experimental manipulations were performed under an atmosphere of dry argon. Solvents were dried and distilled prior to use. Bis(diphenylphosphino)methane (dppm), 1-diphenylphosphino-2-diphenylarsinoethane (ARPHOS), and $Me_3SiN_3$ were commercial materials obtained from Aldrich. Compound Ia was prepared as previously described in Inorg. Chem. 1989, 28, 413 by Katti, K. V. and Cavell, R. G., as set forth in Example 1.

$^1H$, $^{19}F$, $^{31}P$, and $^{29}Si$ NMR spectra were obtained on a Bruker WH 400 instrument (operating at 400.13, 376.40, 161.97, and 79.50 MHz, respectively) using $SiMe_4$, $CFCl_3$, 85% $H_3PO_4$, and $SiMe_4$, respectively, as the external standards. An INEPT sequence was employed to enhance signals in the $^{29}Si$ NMR spectra. In all the spectroscopic studies $CDCl_3$ was used as both the solvent and the internal lock. Positive shifts lie downfield of the standard in all cases. Solution molecular weight measurements were performed in dibromomethane solution with a Mechrolab 301A vapor phase osmometer.

EXAMPLE 1

Synthesis of $Me_3Si\ N=PPh_2(CH_2)PPh_2$ (Ia).

A slurry of $Ph_2P-CH_2-PPh_2$ (5.12 g, 13.33 mmol) in $Me_3SiN_3$ (1.55 g, 13.4 mmol) placed in a round-bottom flask was heated with stirring in an oil bath maintained at 130° C. At the end of 6 hours the clear melt was cooled to 0° C. to give $Me_3SiN=PPh_2(CH_2)PPh_2$ as a microcrystalline solid (yield 6.10 g, 97% M.P. 85° C.). Anal. calculated for $C_{28}H_{31}NP_2Si$: C, 71.33; H, 6.58; N, 2.97. Found C, 71.16; H 6.56 N 2.81 $^{31}P$ NMR $\delta_{P^{III}}-28.20$ (d, $^2J_{pp}=57.7$ Hz) $\delta_{P^V}=-1.38$ (d, $^2J_{pp}=57.7$ Hz) ppm 85% $H_3PO_4$ $^{29}Si$ NMR ($CDCl_3$): $\delta-12.78$ ppm (d, 1, $SiMe_3$ $^2J_{SiP}=21.80$ Hz) MS EI (M/Z):471 (M+, 100%) Solution mol wt.: calcd, 471; found 478.

EXAMPLE 2

Synthesis of $Ph_2PN(Ph)P(S)Ph_2$ (IIa)

A mixture of $Ph_2PN(Ph)PPh_2$ (5.0 g, 10.8 mmol) and elemental sulfur (0.35 g, 10.8 mmol) in n-hexane (50 ml) was heated under reflux for 8 hours then cooled to 25° C. The analytically pure microcrystalline precipitate of $Ph_2PN(Ph)P(S)Ph_2$ was separated by filtration and dried under vacuo. The yield is quantative mp: 142°-144° C., $^{31}P\{^1H\}$ NMR ($CDCl_3$): $\delta_{P^{III}}$ 54.5 ppm $\delta_{P^V}$ 72.4 ppm (85% $H_3PO_4$) $^2J_{pp}=104.6$ Hz. MS (EI m/z)=493 (M+). Analysis calculated for $C_{30}H_{25}NP_2S$: C, 73.02, H. 5.07, N. 2.84. Found: C, 72.94; H. 5.14; N. 2.78.

EXAMPLE 3

Synthesis of $Ph_2PN(Ph)P(Se)Ph_2$ (IIc)

A mixture of $Ph_2PN(Ph)PPh_2$ (2.5 g, 5.4 mmol) and selenium powder (0.43 g, 5.4 mmol) in a mixture of n-hexane (30 ml) and toluene (10 ml) was heated under reflux for 8 hours then cooled to 25° C. and filtered. The clear solution was cooled to 0° C. to give white crystalline analytically pure $Ph_2PN(Ph)P(Se)Ph_2$ in 86% yield; mp: 135°-137° C. $^{31}P\{^1H\}$ $CDCl_3$: $\delta_{P^{III}}$ 55.1 ppm; $\delta_{P^v}$ 72.1 ppm (85% $H_3PO_4$); $^2J_{pp}=110.3$ Hz, $^1J_{PSe}=766.5$ Hz. MS (EI M/Z)=540(M+). Analysis calculated for $C_{30}H_{25}NP_2Se$: C, 66.66; H, 4.63; N. 2.59: Found: C, 66.50; H, 4.70; N, 2.59.

EXAMPLE 4

Synthesis of $Ph_2PN(Ph)P(NC_6F_4CN)Ph_2$ (IIe)

A solution of $N_3C_6F_4CN$ (1.17 g, 5.4 mmol) in dry $CH_2Cl_2$ (15 ml) was added dropwise to a solution of $Ph_2PN(Ph)PPh_2$ (2.5 g, 5.4 mmol) also in $CH_2Cl_2$ (25 ml) at $-78°$ C. with stirring. The reaction mixture which turns yellow during the course of the addition was warmed to 25° C. after the completion of the addition and stirred for 8 hours. The clear yellow solution was filtered and the solvent was removed under vacuum to give microcrystalline $Ph_2PN(Ph)P(NC_6F_4CN)Ph_2$ in 85% yield, MP: 88°-89° C., 1R ($CH_2Cl_2$): (C=N)=2228 $cm^{-1}$. $-p$ $\{^1H\}$ $CDCl_3$: $\delta_{P^{III}}$ 56.5 ppm $\delta_{P^v}$ 22.5 ppm (85% $H_3PO_4$). $^2J_{pp}=89.0$ Hz, $^4J_{P^vF}=3.5$ Hz, $J_{P^{III}F}=10$ Hz, MS (EI M/Z=649 (M+)). Analysis calculated for $C_{37}H_{25}N_3F_4P_2$: C, 68.41: H, 3.85; N, 6.47, Found: C, 67.40; H, 3.83; N, 6.52.

EXAMPLE 5

Synthesis of N-(diphenylphosphino)benzalimine (IIIa).

In a 500 ml 24/40 round bottom flask was placed N-trimethylsilylbenzalimine (8.82 g, 49.8 mmol) and toluene (150 ml). The reaction flask was cooled to 0° C. and chlorodiphenylphosphine (10.99 g, 49.84 mmol) in toluene (50 ml) was added dropwise. The reaction mixture was allowed to sit overnight. Removal of the solvent in vacuo (caution: this compound is thermally unstable in solution, avoid exposure to unnecessary heat for higher yield) produces a yellow sticky solid (13.8 g, 47.7 mmol) which can be carefully recrystallized from acetonitrile. mp=70°-73° C., Analysis: $C_{19}H_{16}NP$ Calculated; C=78.88%, H=5.57%, N=4.84%. Found; C=77.53%, H=5.67%, N=4.61%, $^1H$ NMR (d, $CDCl_3$, TMS); 8.27 ppm, d, $^1H$, $^3J_{HP}=22$ Hz; 7.8—7.4 ppm, m 15H. $^{31}P$ NMR (d, $CDCl_3$, $H_3PO_4$): 49.4 ppm, s.

EXAMPLE 6

Synthesis of p-$(N=C)C_6F_4N=PPh_2CH_2PPh_2$ (Ib).

To a solution of (Ia) (5.123 g, 10.80 m moles) in dry toluene (100 mL) was injected pentafluorobenzonitrile (3.126 g, 16.20 m moles) by using a syringe. The reaction mixture was refluxed for 12 h before the solvent was removed in vacuo to leave a pale yellow solid. The crude product (Ib) was crystallized from acetonitrile to obtain a pure compound (yield 5.59 g, 89%; pale yellow needle-shaped crystals; mp 188° C.). Analysis calculated for $C_{32}H_{22}F_4N_2P_2$: C, 67.10; H, 3.84; N, 4.89. Found: C, 67.13; H, 3.81; N, 4.87. MS (EI, m/z): 572 (M+). $^1H$ NMR ($CDCl_3$): δ 7.27, 7.60, 7.85 (m, 20 H)(TMS); $PCH_2P$ methylene δ 6 3.15 (dd, 2 H, $^2J_{P^vH}=12.50$, $^2J_{P^{III}H}=$ δ 1.15 Hz)(TMS). $^{19}F$ NMR ($CDCl_3$): AA'BB' spin system δ −99.85 ppm vs $CFCl_3$ (m, 2 F), −159.25 ppm vs $CFCl_3$ (m, 2 F).

EXAMPLE 7

Synthesis of p—$NC_5F_4N=PPh_2CH_2PPh_2$ (If).

To a solution of $Me_3SiN=PPh_2CH_2PPh_2$ (Ia) (4.532 g, 9.62 m moles) in dry toluene (100 mL) was injected pentafluoropyridine (2.439 g, 14.40 m moles) by using a syringe. The reaction mixture was refluxed for 20 h before the solvent was removed in vacuo to leave a transparent orange crystalline solid. This crude product was crystallized from acetonitrile to obtain pure compound (If) (yield 4.95 g, 94%; orange cubic crystals; mp 60° C.). Analysis calculated for $C_{30}H_{22}F_4N_2P_2$: C, 65.69; H, 4.01; N, 5.10. Found: C, 65.66; H, 4.10; N, 5.08. MS (EI, m/z): 548 (M+). $^1H$ NMR ($CDCl_3$): δ 7.25, 7.62, 7.87 (m, 20 H); $PCH_2P$ methylene δ 3.17 (dd, 2 H, $^2J_{P^vH}=12.65$, $^2J_{P^{III}H}=1.15$ Hz)(TMS). $^{19}F$ NMR ($CDCl_3$): AA'BB' spin system δ −141.43 ppm (m, 2 F), −155.07 ppm (m, 2 F)($CFCl_3$).

EXAMPLE 8

Synthesis of p-(NC)$C_6F_4$

Synthesis of p-(NC)$C_6F_4N=PPh_2CH_2PPh_2Rh(CO)Cl$.

(CO)Cl.

A solution of p—NC—$C_6F_4N=PPh_2CH_2PPh_2$ (Ib) (0.145 g, 0.25 m moles) in dry dichloromethane (25 mL) was added dropwise at 25° C. to a solution of $[Rh(CO)_2Cl]_2$ (0.049 g, 0.12 m moles) also in the same solvent (25 mL). The mixture was stirred at the same temperature for 4 h before the solvent was removed in vacuo to yield an analytically pure brown crystalline solid product as a dichloromethane solvate (yield, after washing with hexane (5 mL), 0.18 g, 90%; brown microcrystalline; mp 215° C. dec). Analysis calculated for $C_{34}24Cl_3F_4N_2OP_2Rh$: C, 49.55; H, 2.91; N, 3.40; Cl, 12.91. Found: C, 49.53; H, 2.89; N, 3.38; Cl, 12.90. $^1H$ NMR ($CDCl_3$): phenyl rings δ 7.27, 7.65, 7.90 (m 20 H); $PCH_2P$ methylene δ 3.78 (dd, 2 H, $^2J_{HP}=12.0$, 8.20 Hz)TMS. $^{19}F$ NMR ($CDCl_3$): AA'BB' spin system δ −137.27 ppm (m, 2 F), −142.56 ppm (m, 2 F) ($CFCl_3$).

EXAMPLE 9

Synthesis of $NC_5H_4$

Synthesis of $NC_5H_4N=PPh_2CH_2PPh_2Rh(CO)Cl$.

(CO)Cl.

The reaction of $NC_5H_4$—$N=PPh_2CH_2PPh_2$ (If) with $[Rh(CO)_2Cl]_2$ was carried out under similar experimental conditions to those described for in example 8 to obtain the dichloromethane solvate of the Rh complex in 88% yield (yellow microcrystalline; mp 180° C. dec). Analysis calculated for $C_{32}H_{24}Cl_3F_4N_2OP_2Rh$: C, 48.04; H, 1.25; N, 3.50. Found: C, 48.11; H, 1.21; N, 3.47. $^1H$ NMR ($CDCl_3$): phenyl rings δ 7.26, 7.60, 7.88 (m, 20 H); $PCH_2P$ methylene δ 3.75 (dd, 2 H, $^2J_{HP}=12.10$, 7.50 Hz)(TMS). $^{19}F$ NMR ($CDCl_3$): AA'BB' spin system δ −138.15 ppm (m, 2 F), −147.50 ppm (m, 2 F)($CFCl_3$).

EXAMPLE 10

Synthesis of $Me_3SiN=PPh_2(CH_2)_2AsPh_2$ (Io).

A solution of $Me_3SiN_3$ (2.25 g, 19.64 m moles) in toluene (25 mL) was added dropwise at room temperature to a solution of $Ph_2P(CH_2)_2AsPh_2$ (ARPHOS) (7.55 g, 17.08 m moles) also in toluene (100 mL). The mixture was heated under reflux for 16 h before the solvent was removed in vacuo to yield an off-white crystalline solid which was recrystallized from dry acetonitrile to obtain pure compound (Io) (yield 8.75 g, 96%; mp 131° C.). Analysis calculated for $C_{29}H_{33}NAsPSi$: C, 65.79; H, 6.23; N, 2.64. Found: C, 65.76; H, 6.19; N, 2.63. MS(EI, m/z): 5.28 (M+). $^{31}P$ NMR (161.93 MHz in $CDCl_3$, vs 85% $H_3PO_4$): δ 1.83 ppm. $^{29}Si$ NMR (INEPT; 79.5 MHz in $CDCl_3$, vs $Me_4Si$): δ−11.33 (d, $^2J(^{29}Si$-$^{31}P)=19.57$ Hz).

EXAMPLE 11

Synthesis of Arsenic Complexes and Compounds.
(a). $Me_3Si$ (a).
$Me_3SiN = PPh_2(CH_2)_2AsPh_2Rh(CO)Cl$.

(CO)Cl.

A solution of $Me_3SiN=PPh_2(CH_2)_2AsPh_2$(Io) (0.310 g, 0.58 m moles) in dry dichloromethane (50 mL) was added dropwise (20 min) to a solution of $[Rh(CO)_2Cl]_2$ (0.113 g, 0.29 m moles) also in the same solvent. The reaction mixture was stirred at 25° C. for 2 h before the solvent was removed in vacuo to yield an analytically pure dichloromethane solvate of the complex (yield, after washing with hexane (5 mL), 0.43 g, 95%; yellow microcrystalline; mp 165° C. dec). Analysis calculated for $C_{31}H_{35}Cl_3NOAsPRhSi$: C, 47.68; H, 4.48; N, 1.79; Cl, 13.63. Found: C, 47.65; H, 4.46; N, 1.77; Cl, 13.60. $^1$NMR ($CDCl_3$): phenyl rings δ 7.35, 7.55, 7.70 (m, 20 H); $AsCH_2CH_2P$ δ 2.17 (m, 2 H), 2.60 (m, 2 H);

Si(CH$_3$)$_3$ δ 0.05 (s, 9 H ). $^{29}$Si NMR (INEPT; CDCl$_3$ ): δ 6.20 (d, 1 Si, $^2J_{P'Si}$, =5.50 Hz).

(b). The Metallacycles

and N=PPh$_2$(CH$_2$)$_2$AsPh$_2$Ir(cod) were prepared by employing similar experimental conditions to those described above in Example 11a.

yield 82%; yellow microcrystalline; mp 170° C. dec. Analysis calculated for C$_{35}$H$_{38}$Cl$_2$NAsPRh: C, 55.87; H, 5.05; N, 1.86; Cl, 9.43. Found: C, 55.85; H, 5.01; N, 1.84; Cl, 9.49. $^1$H NMR (CDCl$_3$) phenyl rings δ 7.37, 7.60, 7.80 (m, 20 H); AsCH$_2$CH$_2$P δ 2.25 (m, 2 H), δ 2.65 (m, 2 H); cod olefinic δ 5.30 (br, 2 H), 5.45 (br, 2 H); cod methylene δ 2.30 (br, 4 H), 1.70 (br, 4 H)TMS.

yield 85%; brown microcrystalline; mp 190° C. dec. Analysis calculated for C$_{35}$H$_{38}$Cl$_2$NAsPIr: C, 49.93; H, 4.52; N, 1.66; Cl, 8.43. Found: C, 50.01; H, 4.49; N, 1.65; Cl, 8.46. $^1$H NMR (CDCl$_3$): phenyl rings δ 7.35, 7.62, 7.85 (m, 20 H; AsCH$_2$CH$_2$P δ 2.19 (m, 2 H), 2.60 (m, 2 H); cod olefinic δ 5.32 (br, 2 H), 5.40 (br, 2 H); cod methylene δ 2.30 (br, 4 H), 1.72 (br, 4 H)TMS.

EXAMPLES 12 and 13

[Rh(CO)$_2$Cl]$_2$ (0.031 g, 0.079 m moles) was dissolved in methanol (5 ml) in a 50 ml pop bottle reactor maintained under an argon atmosphere. To the stirred solution the difunctional ligand Ph$_2$P—(CH$_2$)$_2$—Ph$_2$P=N—SiMe$_3$ (Ic) (0.0812 g, 0.140 m moles) was added. The mixture was stirred for 10 minutes. Then Ph$_3$P (0.214 g, 0.82 m moles) was added followed by lithium acetate (0.412 g, 4.0 m moles), CH$_3$I (1 ml, 15 m moles) and finally methanol (5 ml). Then the tube was flushed with carbon monoxide and sealed. The reactor was then placed in an oil bath maintained at 80°-85° C. and pressurized with CO to 40 p.s.i.g. The reaction was followed by taking samples at determined intervals of time by momentarily stopping the reaction and removing a sample with a syringe.

In Table I data is presented for the run along with the data for a similar run with no Ph$_3$P added. The rates were determined by measuring the amount of methylacetate formed during the run using gas chromatograph.

TABLE I

| Ex. No. | Rh/Ligand/Ph$_3$P Ratio | Reaction Rate |
|---|---|---|
| 12 | 1:2:10 | 2.0 g moles/l/hr. |
| 13 | 1:10:0 | 2.5 g moles/l/hr. |

When the difunctional ligand is used as the excess ligand the reaction rate is higher, even though the total Rh:Ligand ratio is lower.

EXAMPLE 14

[Rh(CO)$_2$Cl]$_2$ (0.0124 g, 0.032 m moles) was dissolved in methanol (5 ml) in a 50 ml pop bottle reactor maintained under an argon atmosphere. To the stirred solution the difunctional ligand

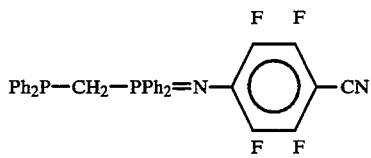

(0.134 g, 0.234 m moles) was added. The mixture was stirred for 10 minutes. Then lithium acetate (0.244 g, 2.4 m moles), CH$_3$I (1 ml, 16 m moles) and finally methanol (5 ml) were added. Then the tube was flushed with carbon monoxide and sealed. The reactor was then placed in an oil bath maintained at 85°-90° C. and pressurized with CO to 40 p.s.i.g. The reaction was followed by taking samples at determined intervals of time by momentarily stopping the reaction and removing a sample with a syringe.

In Table II data is presented for the run.

TABLE II

| Ex. No. | Rh/Ligand Molar Ratio | Reaction Rate |
|---|---|---|
| 14 | 1:7 | 1.2 g moles/l/hr. |

EXAMPLE 15

[RhCl(CO)$_2$]$_2$ (0.0131 g, 0.033 m moles) was dissolved in methyl (5 ml) acetate in a 50 ml pop bottle reactor maintained under an argon atmosphere. To the stirred solution of the difunctional ligand

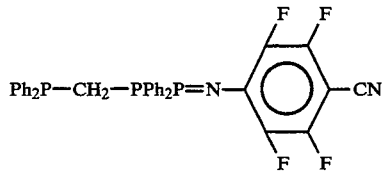

(0.135 g, 0. 236 m moles) was added. The mixture was stirred for 10 minutes. Then lithium acetate (0.218 g, 2.1 m moles), CH$_3$I (1 ml, 16 m moles) and methanol (5 ml) were added. The tube was flushed with carbon monoxide and sealed. The reactor was then placed in an oil bath maintained at 85°-90° C. and pressurized with CO to 40 p.s.i.g. The reaction was followed by taking samples at determined intervals of time by momentarily stopping the reaction and removing a sample with a syringe.

Data for the run is presented in Table III:

TABLE III

| Ex. No. | Rh/Ligand molar ratio | Reaction Rate |
|---|---|---|
| 15 | 1:7 | 0.6 g moles/l/hr. |

Comparing the rate to example number 14, changing solvent to methyl acetate seems to lower the reaction rate under the experimental conditions employed.

EXAMPLE 16

A series of runs were carried out using [Rh(CO)$_2$Cl]$_2$ as the metal source, Ph$_2$P—(CH$_2$)$_2$—PPh$_2$=N—SiMe$_3$ (Ic) as the ligand and Ph$_3$P as the excess ligand, employing conditions as described in examples 12 and 13.

The results obtained are presented in Table IV:

TABLE IV

Turnover Number* As a Function of the Moles Of Rhodium Compound

| Rhodium Compound** | Turnover Number |
| --- | --- |
| 0.026 × 10$^{-3}$ moles | 730 |
| 0.097 × 10$^{-3}$ moles | 223 |
| 0.145 × 10$^{-3}$ moles | 200 |
| 0.168 × 10$^{-3}$ moles | 125 |
| 0.195 × 10$^{-3}$ moles | 95 |

*measured for the reaction of methanol with carbon monoxide in the presence of [Rh(CO)$_2$Cl]$_2$ (× m moles) + Ph$_2$—CH$_2$—CH$_2$—PPh$_2$=NSiMe$_3$(2 × m moles) + Ph$_3$P (0.77 m moles) + Lithium acetate (4 m moles)
**as monomeric species in solution The data indicate that for lower concentration of the catalyst, the turnover numbers are higher under the experimental conditions employed.

EXAMPLE 17

Cobalt acetate tetra hydrate (0.144 g, 0.6 m mole) was added to methanol (5 ml) in a 50 ml pop bottle reactor maintained under an argon atmosphere. To the stirred solution the difunctional ligand Me$_3$Si—N=PPh$_2$—CH$_2$—CH$_2$—PPh$_2$=N—SiMe$_3$ (0.418 g, 0.73 m mole) was added. The mixture was stirred for 10 minutes. Then Ph$_3$P (0.203 g, 0.78 m mole) lithium acetate (0.424 g, 4.2 m mole), CH$_3$I (1 ml, 16 m moles) and methanol (5 ml) were added. The tube was flushed with carbon monoxide and sealed. The reactor was then placed in an oil bath maintained at 85°-90° C. and pressurized with CO to 40 p.s.i.g. At the end of 20 hours the reaction mixture contained 5% of CH$_3$COOCH$_3$, indicating a lower catalytic activity by the cobalt complex, compared to the Rh complex.

EXAMPLE 18

Nickel acetate tetra hydrate (0.145 g, 0.6 m mole) was added to methanol (5 ml) in a 50 ml pop bottle reactor maintained under an argon atmosphere. To the stirred solution the difunctional ligand Me$_3$Si—N=PPh$_2$—CH$_2$—CH$_2$—PPh$_2$=N—SiMe$_3$ (0.453 g, 0.79 m mole) was added. The mixture was stirred for 10 minutes. Then Ph$_3$P (0.198 g, 0.76 m mole), lithium acetate (0.467 g), CH$_3$I (1 ml, 16 m mole) and methanol (5 ml) were added. The tube was flushed with carbon monoxide and sealed. The reactor was then placed in an oil bath maintained at 84°-90° C. and pressurized with CO to 40 p.s.i.g. At the end of 20 hours the reaction mixture contained 5.9% of CH$_3$COOCH$_3$, indicating a lower catalytic activity by the nickel complex compared to the Rh complex.

EXAMPLE 19

[Rh(CO)$_2$Cl]$_2$ (0.030 g, 0.08 m mole) was added to methanol (5 ml) in a 50 ml pop bottle reactor maintained under an argon atmosphere. To the stirred solution of the difunctional ligand

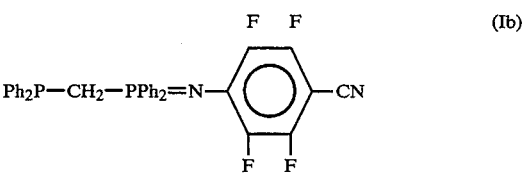

(0.253 g, 0.44 mole) was added. The mixture was stirred for 10 minutes. Then the promotor

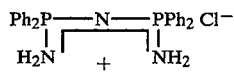

(1.025 g, 2.3 m mole), CH$_3$I (1 ml, 16 m mole) and methanol (5 ml) were added. The tube was flushed with carbon monoxide and sealed. The reactor was then placed in an oil bath maintained at 84°-90° C. and pressurized to 40 p.s.i.g. with CO. The reaction rate was measured by monitoring the concentration of the methyl acetate formed during the run. The initial rate of formation of methyl acetate was found to be 0.9 g moles/l/hr.

EXAMPLE 20

[Rh(CO)$_2$Cl]$_2$ (0.018 g, 0.046 mmol) was added to methanol (5 ml) in a 50 ml pop bottle reactor maintained under an argon atmosphere. To the stirred solution Me$_3$SiN=PPh$_2$(CH$_2$)$_5$PPh$_2$ (Il) (0.062 g, 0.121 mmol) was added. The mixture was stirred for 10 minutes. Then Ph$_3$P (0.200 g, 0.76 mmol), LiOAc (0.206 g, 2 mmol) and CH$_3$I (1 ml, 16 mmol) and CH$_3$OH (5 ml) were added. The reator was then flushed with CO and sealed. The reactor was then placed in an oil bath maintained at 90° C. and pressurized with CO to 40 p.s.i.g.. After 45 hours the reaction mixture contained 30.9 molar % of CH$_3$COOCH$_3$.

EXAMPLE 21

[Rh(CO)$_2$Cl]$_2$ (0.013 g, 0.033 mmol) was added to methanol (5 ml) in a 50 ml pop bottle reactor maintained under an argon atmosphere. To the stirred solution Me$_3$SiN=PPh$_2$ (CH$_2$)$_3$—PPh$_2$ (Ig) (0.041 g, 0.083 mmol) was added. The mixture was stirred for 10 minutes. Then Ph$_3$P(0.200 g, 0.26 mmol), LiOAc (0.206 g, 2 mmol), CH$_3$I (1 ml, 16 mmol, and CH$_3$OH (5 ml) were added. The tube was then flushed with CO and sealed. The reactor was then placed in an oil bath maintained at 90° C. and pressurized with CO to 40 p.s.i.g. After 52 hours 13 mole % of the reactor mixture was CH$_3$COOCH$_3$.

EXAMPLE 22

[Rh (CO)$_2$Cl]$_2$ (0.019 g, 0.049 mmol) was added to methanol (5 ml) in a 50 ml pop bottle reactor maintained under an argon atmosphere. To the stirred solutions Ph$_2$P(S)—N(Ph)—PPh$_2$ (IIa) (0.124 g, 0.251 mmol) was added. The mixture was stirred for 10 minutes. Then LiOAc (0.240 g, 2.6 mmol) CH$_3$I (1 ml, 16 mmol) and CH$_3$OH (5 ml) were added. The reactor was then flushed with CO and sealed. The reactor was then placed in an oil bath maintained at 85° C. Then it was pressurized with CO to 40 p.s.i.g. After 24 hours 89.2% of CH$_3$OH was converted into CH$_3$COOH and CH$_3$COOCH$_3$

EXAMPLE 23

[Rh(CO)$_2$Cl]$_2$ (0.016 g, 0.04 mmol) were added to methanol (5 ml) in a 50 ml pop bottle reactor maintained under an argon atmosphere. To the stirred solution Ph$_2$P—N=C(H)Ph (IIIa) (0.124 g) was added. The mixture was stirred for 10 minutes. Then pyridine (0.5 ml), CH$_3$I (1 ml, 16 mmol) and CH$_3$OH (5 ml) were added. The reactor was then placed in an oil bath maintained at 80°–85° C. Then it was pressurized with CO to 40 p.s.i.g. After 45 hours, 84% of methanol was converted into methylactetate and acetic acid.

EXAMPLE 24

(Ph$_3$P)$_3$RhCl (0.047 g, 0.05 mmol) was added to methanol (5 ml) in a 50 ml pop bottle reactor maintained under an argon atmosphere. To the stirred solution Ph$_2$P—N=C(H)Ph (0.208 g, 0.72 mmol) was added. The mixture was stirred for 10 minutes. Then LiOAc (0.208 g, 2.0 mmol), CH$_3$I (1 ml, 16 mmol) and CH$_3$OH were added. The reactor was then flushed with CO and sealed. The reactor was then flushed in an oil bath maintained at 85° C. and pressurized with CO to 40 p.s.i.g. After 44.5 hours 37.5 mole % of CH$_3$OH was converted into CH$_3$COOCH$_3$ and CH$_3$OCH$_3$.

EXAMPLE 25

[Rh(CO)$_2$Cl]$_2$ (0.032 g, 0.08 mmol) was added to methanol (5 ml) in a 50 ml pop bottle reactor maintained under an argon atmosphere. To the stirred solution

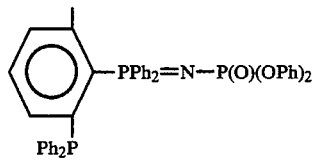

(0.320 g, 0.46 mmol) was added. The mixture was stirred for 10 minutes. Then LiOAc (0.432 g, 4.2 mmol), CH$_3$I (1 ml, 16 mmol) and CH$_3$OH (5 ml) were added. The reactor was then flushed with CO and sealed. The reactor was then placed in an oil bath maintained at 90° C. and pressurized with CO to 40 p.s.i.g. After 41 hours 27.6 mole % of CH$_3$OH was converted into CH$_3$COOCH$_3$.

EXAMPLE 26

[Rh(CO)$_2$Cl]$_2$ (0.017 g, 0.04 mmol) was added to methanol (5 ml) in a 50 ml pop bottle reactor maintained under an argon atmosphere. To the stirred solution Ph$_2$P—N=C(H)Ph (0.237 g, 0.82 mmol) was added. The mixture was stirred for 10 minutes. Then morpholine (0.5 ml, 5.7 mmol), CH$_3$I (1 ml, 16 mmol) and CH$_3$OH (5 ml) were added. The reactor was then flushed with CO and sealed. The reactor was then placed in an oil bath maintained at 85° C. and pressurized with CO to 40 p.s.i.g. After 55 hours 96 mole % of methanol was converted into CH$_3$COOCH$_3$ (56%) CH$_3$COOH (41%) and CH$_3$OCH$_3$ (3%).

EXAMPLE 27

[Rh(COD)Cl]$_2$ (0.024 g, 0.049 mmol) was added to methanol (5 ml) in a 50 ml pop bottle reactor maintained under an argon atmosphere. To the stirred solution PPh$_2$—N(Ph)—P(S)Ph$_2$ (0.116 g, 0.251 mmol) was added. Then the mixture was stirred for 10 minutes. Then LiOAc (0.249 g, 2.4 mmol), CH$_3$I (1 ml, 16 mmol) and CH$_3$OH (5 ml) were added. The reactor was then flushed with CO and sealed. The reactor was then placed in an oil bath maintained at 90° C. and pressurized with CO to 40 p.s.i.g. After 24 hours 89 mole % of the CH$_3$OH was converted into CH$_3$COOCH$_3$ (74%), CH$_3$COOH (23%) and CH$_3$OCH$_3$ (3%).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, are hereby incorporated by reference. Also incorporated by reference is applicants' parent application Ser. No. 07/575,903, filed Aug. 31, 1990, of which this application is a continuation-in-part.

The embodiments of the invention in which an exclusive property or privilege is claimed are defined as follows:

1. In a catalytic process for the carbonylation of methanol to one or more of acetic acid and its esters, the improvement comprising:

reacting methanol and carbon monoxide using a transition metal catalyst precursor having a phosphorus-nitrogen chelated ligand attached to the metal as a catalyst the catalyst precursor having the general formula:

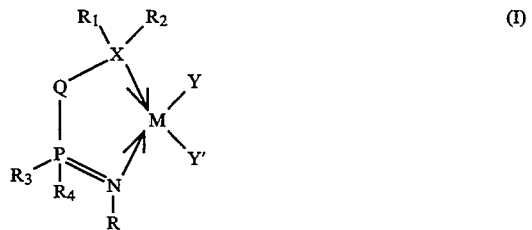

(I)

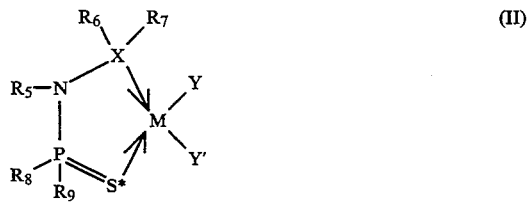

(II)

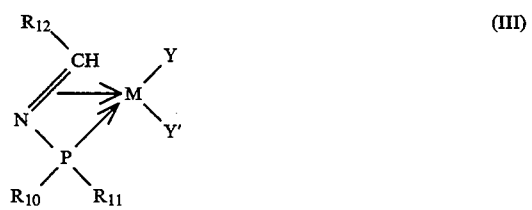

(III)

wherein

M is a Group VIII B transition metal

Y, Y' are same or different, selected from CO, Cl$^-$, phosphines and olefinic hydrocarbons $R_{1-4}$, $R_{6-12}$ are same or different substituted or unsubstituted aryl groups Q is selected from a benzene ring connected to P and X in the o-positions, an olefin connected to P and X across the double bond, or (CH$_3$)CH X is P or As R = a substituted aromatic ring

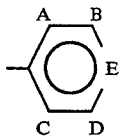

where A, B, C or D are selected from F, H, NO$_2$, CN and alkyl and E is endocyclic nitrogen, a C—NO$_2$ group of a C—CN group, or isomers thereof, or R=SiMe$_3$ or TiCl$_2$Cp, where Me is methyl, and Cp is cyclopentadienyl, or P(O)(OPh)$_2$, where Ph is a phenyl ring, $R_5$ is aryl or alkyl, and S* is S, Se, O or N—R, R being as defined hereinabove.

2. The improved process of claim 1, wherein M is selected from Rh, Co or Ni.

3. The improved process of claim 1, wherein the catalyst precursor has the formula I wherein M is selected from Rh, Co and Ni, $R_{1-4}$ are phenyl groups, and Q is a benzene ring, an olefin or (CH$_3$)CH, as defined in claim 1.

4. The improved process of claim 3 wherein, the catalyst has the formula I in which X is P; R is the substituted aromatic ring wherein A, B, C and D are selected from F and NO$_2$; and, if Q is an olefin, it has the formula R'C=CR"(R',R"=H, CH$_3$, or other alkyl).

5. The improved process of claim 1, wherein:
(a) the catalyst precursor has the formula II, wherein $R_5$ is phenyl or methyl and S* is S, Se or N—R and R is as defined in claim 1, or
(b) the catalyst precursor has the formula III, wherein $R_{10-12}$ are phenyl.

6. The process of claim 1, wherein a promoter is used selected from lithium acetate, sodium tetraphenyl borate, Ph$_4$AsCl, LiCl, LiI, KPF$_6$, Et$_3$N, pyridine, quinoline, morpholine or a Bezman salt.

7. The process of claim 3, wherein a promoter is used selected from lithium acetate, sodium tetraphenyl borate, Ph$_4$AsCl, LiCl, LiI, KPF$_6$, Et$_3$N, pyridine, quinoline, morpholine or a Bezman salt.

8. The process of claim 5, wherein a promoter is used selected from lithium acetate, sodium tetraphenyl borate, Ph$_4$AsCl, LiCl, LiI, KPF$_6$, Et$_3$N, pyridine, quinoline, morpholine or a Bezman salt.

9. The improved process of claim 1, wherein the catalyst precursor is of formula II or III.

10. A transition metal complex catalyst precursor having a phosphorus-nitrogen chelated ligand attached to the metal and having the general formula

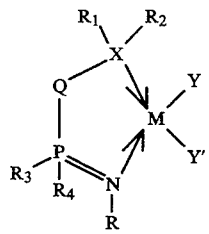

(I)

-continued

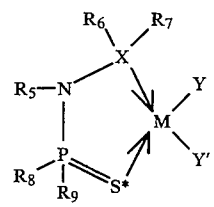

(II)

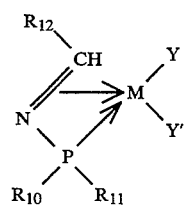

(III)

wherein

M is a Group VIII B transition metal

Y, Y' are same or different, selected from CO, Cl$^-$, phosphines and olefinic hydrocarbons $R_{1-4}$, $R_{6-12}$ are same or different substituted or unsubstituted aryl groups Q is selected from a benzene ring connected to P and X in the o-positions, an olefin connected to P and X across the double bond, or (CH$_3$)CH X is P or As R is a substituted aromatic ring,

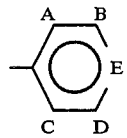

where A, B, C, or D are selected for F, H, NO$_2$, CN and alkyl and E is endocyclic nitrogen, a C—NO$_2$ group of a C—CN group, or isomers thereof, or R=SiMe$_3$ or TiCl$_2$Cp, where Me is methyl, and Cp is cyclopentadienyl, or P(O)(OPh)$_2$, where Ph is a phenyl ring, $R_5$ is aryl or alkyl, and S* is S, Se, O or N—R, R being as defined hereinabove.

11. A catalyst precursor of claim 10, wherein M is selected from Rh, Co or Ni.

12. A catalyst precursor of claim 10 which has the formula I, wherein M is selected from Rh, Co or Ni, $R_{1-4}$ are phenyl groups and Q is a benzene ring, an olefin or (CH$_3$)CH, as defined in claim 10.

13. A catalyst precursor of claim 12, which is of the formula I and in which X is P; R is a substituted aromatic ring,

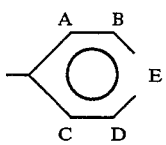

A—E being defined as in claim 10, and if Q is an olefin, it has the formula R'C=CR"(R',R"=H, CH$_3$, or other alkyl).

14. A catalyst precursor of claim 10;
(a) which is of the formula II, wherein $R_5$, is phenyl or methyl $R_{6-9}$ are phenyl and S* is S, Se or NR, where R is a substituted aromatic ring

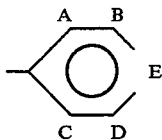

A—E being defined in claim 10, or (b) which is of the formula III, wherein R₁₀₋₁₂ are selected from hydrogen, phenyl or substituted phenyl.

15. A catalyst precursor as claimed in claim 10, which is of the general formula II or III.

16. A phosphorus-nitrogen chelating ligand having the general formula

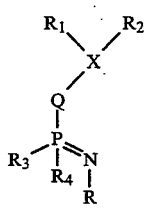 (I')

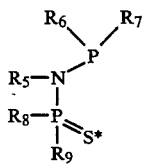 (II')

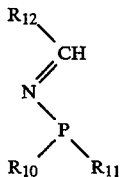 (III')

wherein

R$_{1-4}$, R$_{6-12}$ are same or different substituted or unsubstituted aryl groups Q is selected from a benzene ring connected to P and X in the o-positions, an olefin connected to P and X across the double bond, or (CH₃)CH X is P or As R is a substituted aromatic ring

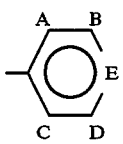

where A, B, C or D are selected for F, H, NO₂, CN and alkyl and E is endocyclic nitrogen, a C—NO₂ group of a C—CN group, or isomers thereof, or R=SiMe₃ or TiCl₂Cp, where Me is methyl, Cp is cyclopentadienyl, or P(O)(OPh)₂, where Ph is a phenyl ring, R₅ is aryl or alkyl, and S* is S, Se, O or N—R, R being as defined hereinabove.

17. A ligand as claimed in claim 16, which is of the general formula II or III.

18. A ligand having the general formulae:

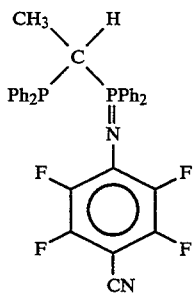 (Im)

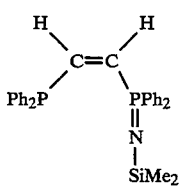 (In)

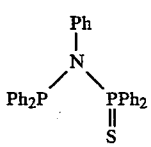 (IIa)

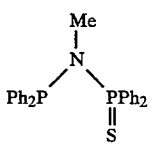 (IIb)

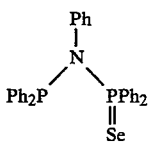 (IIc)

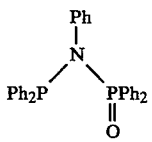 (IId)

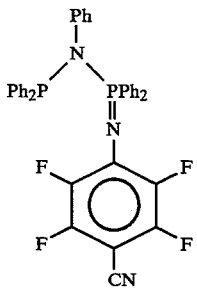 (IIe)

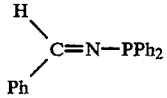 (IIIa)

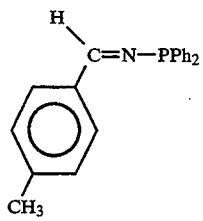 (IIIb)

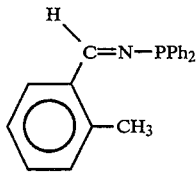
19. A ligand as claimed in claim 18, which is of the general formula IIa–IIc or IIIa–IIIc.
* * * * *